United States Patent [19]

Bailey

[11] 4,252,782

[45] Feb. 24, 1981

[54] TEST FOR ASSESSING THE UNSATURATED BINDING CAPACITY OF SERUM PROTEINS WHICH BIND THYROID HORMONES

[75] Inventor: Anne L. Bailey, Springfield, Va.

[73] Assignee: Meloy Laboratories, Inc., Springfield, Va.

[21] Appl. No.: 947,056

[22] Filed: Sep. 29, 1978

[51] Int. Cl.³ .................... G01N 33/48; A61K 43/00; G01T 1/00; B65D 71/00

[52] U.S. Cl. .......................................... 424/1; 424/12; 23/230 B; 422/61

[58] Field of Search .................... 424/1, 12; 23/230 B; 422/61

[56] References Cited

U.S. PATENT DOCUMENTS

| | | |
|---|---|---|
| 2,531,427 | 11/1950 | Hauser ................................ 260/448 |
| 3,666,854 | 5/1972 | Eisentraut ............................... 424/1 |
| 3,743,482 | 7/1973 | Eisentraut ............................... 424/1 |
| 3,775,615 | 11/1973 | Eisentraut ............................... 424/1 |
| 3,776,698 | 12/1973 | Eisentraut ........................ 23/230 B |
| 3,947,564 | 3/1976 | Shannon et al. ........................ 424/1 |
| 3,996,162 | 12/1976 | McCall ................................. 252/430 |

*Primary Examiner*—Benjamin R. Padgett
*Assistant Examiner*—Christine M. Nucker
*Attorney, Agent, or Firm*—Shapiro and Shapiro

[57] ABSTRACT

An improved test for assessing the unsaturated binding capacity of serum proteins which bind thyroid hormones employs a clay-organic complex for adsorbing a free radioactive hormone fraction. The sorbent, an organically modified montmorillonite, provides better separation of thyroid states and may be employed in smaller amounts than prior sorbents employed in comparable tests.

16 Claims, No Drawings

TEST FOR ASSESSING THE UNSATURATED BINDING CAPACITY OF SERUM PROTEINS WHICH BIND THYROID HORMONES

BACKGROUND OF THE INVENTION

This invention relates to an improved test for assessing the unsaturated binding capacity of serum proteins which bind thyroid hormones and is more particularly concerned with the use of an improved sorbent in such a test.

The thyroid gland synthesizes triiodothyronine (T3) and thyroxine (T4) and releases them into the circulation, where approximately 99.9 percent of these hormones are bound to serum proteins and the remaining small fractions of the thyroid hormones (T3 and T4) circulate in free form. Due to the influence that T3 and T4 have on the metabolic processes, these naturally occuring iodinated amino acids have been the subject of many investigations by thyroid physiologists. From these investigations, the protein components in blood serum which bind the thyroid hormones have been identified and characterized.

Further studies have shown that various diseases, genetic abnormalities, and drugs can alter the concentrations or affinities of the various binding proteins, which sometimes will cause a concurrent rise or fall in the free or unbound hormone level. Due to the profound catabolic effects that the free thyroid hormones exhibit, an assessment of the binding capacity of the serum proteins is often routinely performed as part of a thyroid profile.

At least three serum protein fractions which have different affinities and capacities for thyroxine have been identified by reverse flow paper electrophoresis. Thyroxine binding globulin (TBG) has the highest affinity for T4 and binds 65 to 75% of circulating hormone; albumin has a low affinity and binds only about 10% of the hormone; and thyroxine binding prealbumin (TBPA) has an intermediate affinity for T4 and binds about 15 to 25% of the hormone.

It has been shown that triiodothyronine binds less firmly but in different degrees to the same thyroxine binding proteins. Approximately 70% of the T3 is bound to TBG; 30% is bound to albumin; and a non-detectable amount to TBPA.

The metabolic processes are regulated entirely by the small amounts of free T3 and T4 in circulation. Therefore, the best measure of the thyrometabolic status would be a free hormone level. Presently, the procedures which are available for assessing the levels of free thyroid hormones are very time-consuming and cumbersome to perform. As early as 1965, Clark and Horne demonstrated an indirect method for the estimation of free T4 levels by using the total T4 level and the level of unsaturated binding proteins (T3 Uptake).

A T3 Uptake test is a qualitative assessement of the unsaturated binding capacity of the serum proteins which bind the thyroid hormones. In hypothyroidism, the thyroid hormone levels are low, leaving the binding proteins relatively unsaturated. While in hyperthyroidism, the thyroid hormone levels are elevated, causing a high degree of saturation of the binding proteins.

The first attempt to measure the unsaturated binding capacity was described by Hamolsky in 1957. The test was performed by adding radioactive T3 to a sample of whole blood and measuring the uptake of labelled T3 by the red blood cells. The Hamolsky red blood cell uptake test provided an important in vitro clinical tool, but it had severe limitations caused by variations in the washing technique.

Mitchell taught the use of an ion exchange resin and resin sponge to bind the radioactive T3 not bound to the serum proteins. This method of separation suffered from time and temperature dependence. Since then, various other adsorbents such as coated charcoal, silicates, Sephadex ®, and organic polymers have been utilized as separating agents in T3 uptake tests, all of which have disadvantages.

The following is a list of desirable characteristics of a sorbent for use in a T3 uptake or similar test:
1. Sorbent reaction should not be temperature dependent over a temperature range usually encountered in laboratories.
2. Time dependence should allow the sorbent reaction to reach equilibrium in 15 to 20 minutes and remain stable for at least 60 minutes.
3. Addition of the sorbent should be capable of being carried out by pipetting a suspension of the sorbent or by inserting a sorbent tablet. Ideally, the material should remain in suspension for 30 minutes or longer without any further mixing, or be easily tableted.
4. The sorbent should be stable in suspension or tablet form for at least four months or longer.
5. The sorbent should be easily separated from the reaction mixture by usual laboratory methods, such as centrifugation at 1500 g or less and decantation.
6. The sorbent should not precipitate serum proteins, since both the free and bound $^{125}$I-T3 would be adsorbed and no separation would be achieved.
7. The sorbent should not be toxic or caustic.
8. The sorbent should not react with glass or polystyrene, since most tests are performed in test tubes made of these materials.
9. The sorbent should not be prohibitively expensive.

The sorbents employed in the present invention meet these criteria.

BRIEF DESCRIPTION OF THE INVENTION

In summary, it has been discovered, in accordance with the present invention, that surprising substantially improved performance may be achieved, in a test for assessing the unsaturated binding capacity of serum proteins which bind the thyroid hormones, by the use of a sorbent that is a clay-organic complex, more specifically an organically modified mortmorillonite produced by the substitution of organic cations for the exchangeable cations present on the clay surfaces. It has been found that such sorbents may be employed in much smaller quantities than silicate sorbents employed heretofore, to provide unexpected better separation of thyroid states, without activation of the sorbent. Moreover, when suitable gums, such as guar gums, are added to an appropriately buffered clay-organic sorbent in accordance with the invention, the sorbent remains suspended in water for long periods of time and does not require constant mixing during the test procedure.

DETAILED DESCRIPTION OF THE PREFERRED EMBODIMENTS

U.S. Pat. No. 3,666,854, issued May 30, 1972 to Eisentraut, discloses a thyroid hormone test employing inorganic crystalline sorbent materials, including montmorillonites. Such sorbents require heat activation, and constant mixing while the sorbent is added to the reaction mixture. In accordance with the present invention, organically modified montmorillonite sorbents are employed, which do not require heat activation (or stabilization), which, when admixed with suitable gums, may be employed without constant mixing, and, most importantly, which produce better separation of thyroid states than the previously employed inorganic montmorillonite sorbents, even when used, quite effectively, in much smaller quantities than such prior sorbents. The invention employs a class of materials previously employed for entirely different purposes and applications, such as:

(1) preparation of temperature-resistant greases by dispersing about 5-7% of these products in a mineral oil;
(2) thickening of paint with a related increase of quality by delaying the separation of the pigments;
(3) thickening of paint thinners and solvents; and
(4) putties, fireproof varnishes, printing inks, vinyl products for molding and coating, plastisols and plastigels, waxes, resins, hydraulic fluids, polishes.

Prior applications of the materials utilize their rheological, gelling, and thixotropic properties, for example, which would not suggest the use of such materials in the tests to which the present invention relates. Indeed, the types of applications in which such materials have been employed previously would not only fail to suggest the utility of those materials in the environment of the present invention but would steer away from such use.

The present invention is based upon the use of certain clay-organic complexes in tests for assessing the unsaturated binding capacity of serum proteins for thyroid hormones and upon the discovery of the surprisingly greater separation of thyroid hormone states and other unexpected advantages achieved by the use of such materials. More particularly, the invention employs dioctahedral minerals (clays) of the montmorillonite class [the general formula of which may be written: $RMgAl_5 Si_{12}O_{30} (OH)_6 \cdot nH_2O$,] where R represents exchangeable bases. The improved results are all the more surprising because organically modified hectorite, a trioctahedral mineral reportedly useful in adsorbing proteins, alkaloids, and cationically charged organic and inorganic materials, does not appear to produce such results.

Organically modified clay useful in the present invention may be prepared as described, for example, in U.S. Pat. No. 2,531,427, issued Nov. 28, 1950 to Hauser, incorporated herein by reference. Hauser describes the reaction of certain high base-exchange clays, such as the montmorillonites, with "onium" compounds, including, for example, quaternary ammonium compounds, to produce products which Hauser suggests may be called "high-swelling" oniumbentonites. The organically modified clays produced by Hauser appear to have been principally intended to form gels in organic liquids.

Van Olphen in "An Introduction to Clay Colloid Chemistry," Second Edition (Wiley), also incorporated herein by reference, describes a mechanism by which organic cations are adsorbed on the negative face surfaces of clays such as the montmorillonites, the principal clay mineral of bentonite rock. In such clays there is an excess of negative layer charge that is compensated by the adsorption on the layer surfaces of inorganic cations which may be exchanged with other cations. When an amine salt or quaternary ammonium salt or base, for example, is added to a clay-water suspension, the organic cations replace the exchangeable cations which were originally present on the clay surfaces. The amino groups become strongly attached to the clay surfaces, and the hydrocarbon chains attach themselves to the clay surfaces and displace the previously adsorbed water molecules, producing a clay-organic complex. Suitable examples of such clays are available commercially from N.L. Industries, Inc., Industrial Chemicals Division, Hightstown, New Jersey, and are sold under the trademarks BENTONE 14, BENTONE 27, BENTONE 34, BENTONE 38, and RHEOTONE SA-38. All of these materials are organically modified montmorillonite clays and, as will appear more fully below, may be employed successfully in accordance with the invention. The literature of N.L. Industries, Inc. lists the following typical properties of the various materials.

| BENTONE 14 (A Tetraalkyl Ammonium Smectite) Typical Properties | |
|---|---|
| Color | Light Tan |
| Form | Finely divided powder |
| Density (gm/cm$^3$) | 2.3 |
| (lb/U.S. gal) | 19.2 |
| Bulking value (U.S. gal/lb) | 0.0521 |

| BENTONE 27 (A Trialkylaryl Ammonium Smectite) Typical Properties | |
|---|---|
| Color | Creamy-white |
| Form | Finely divided powder |
| Specific Gravity, 25° C. | 1.8 |
| Weight per U.S. Gallon, lbs. | 15.0 |
| Apparent Density (uncompacted), lbs/U.S. gal. | 2.8 |
| Fineness, through No. 200 sieve, % | 95 |
| Particle Size, maximum dimension, microns (dispersed) | 0.8 by 0.8 by 0.0025 |
| Moisture Content, max., % | 3.5 |
| Loss on Ignition, max., % | 3.5 |
| Lead Content, ppm | <10 |
| Arsenic Content, ppm | <2 |

| BENTONE 34 (A Tetraalkyl Ammonium Smectite) Typical Properties | |
|---|---|
| Color | Very light cream |
| Form | Finely divided powder |
| Specific Gravity, 25° C. | 1.7 |
| Weight per U.S. Gallon, lbs | 14.2 |
| Apparent Density (uncompacted), lbs/U.S. gal. | 2.8 |
| Fineness, through No. 200, sieve, % | 95 |
| Particle Size, maximum dimension, microns (dispersed) | 0.8 by 0.8 by 0.0025 |
| Moisture Content, max., % | 3.5 |
| Loss on Ignition, max., % | 40.5 |
| Lead Content, ppm | <10 |
| Arsenic Content, ppm | <3 |

| BENTONE 38 (A Tetraalkyl Ammonium Smectite) Typical Properties | |
|---|---|
| Color | Creamy-White |
| Form | Finely divided powder |
| Specific Gravity, 25° C. | 1.7 |
| Weight per U.S. Gallon, | |

| | |
|---|---|
| lbs | 14.2 |
| Apparent Density (uncompacted), lbs/U.S. gal. | 3.1 |
| Fineness, through No. 200 sieve, % | 95 |
| Particle Size, maximum dimension, microns (dispersed) | 0.8 by 0.8 by 0.0025 |
| Moisture Content, max., % | 3.5 |
| Loss on Ignition, max., % | 40.5 |
| Lead Content, ppm | <10 |
| Arsenic Content, ppm | <3 |

| RHEOTONE SA-38 Typical Properties | |
|---|---|
| Color | Creamy White |
| Form | Finely divided powder |
| Density (gm/cm$^3$) | 1.63 |
| (lb/U.S. gal) | 13.6 |
| Bulking Value (U.S. gal/lb) | 0.0735 |

A sorbent employed in tests in accordance with the present invention may be prepared from the commercially available materials in the following manner:

1. A convenient amount of BENTONE 14, for example, (3 mg/ml) is sprinkled onto the surface of a convenient amount of 0.05 molar sodium barbital (in water) buffer (pH 8.6) and allowed to settle into suspension.
2. After the organic sorbent has settled, the suspension is mixed with a Virtis overhead mixer for 72 hours at room temperature, for a large batch of 16 to 100 liters. This facilitates thorough mixing and a homogeneous batch.
3. After the mixing, an appropriate amount of Jaguar A-2S (0.2%) or other suitable gum is added to the mixture while the mixture is further mixed, and the mixture is then stirred for an additional 48 hours to assure a homogeneous suspension and bottled while mixed. It is now ready for use.

The sorbent may be employed as part of a test kit including the following reagents:

1. T3 uptake normal human serum control with 0.1% sodium azide preservative, 4 ml per bottle.
2. T3 uptake liquid adsorbent of the invention containing 0.1% sodium azide, 100 ml per bottle.
3. T3 uptake $^{125}$I-T3 buffer reagent containing 0.05 M sodium barbital buffer, 0.1% sodium azide, $^{125}$I labelled triiodothyronine diluted to contain ten microcuries or less of $^{125}$I-T3 with 0.02% bovine serum albumin, 100 ml per bottle.

In general, a T3 uptake test employing the sorbent of the invention may be performed by adding sufficient $^{125}$I labelled triiodothyronine to a serum sample to saturate the binding sites on the serum proteins. The free or unbound $^{125}$I-T3 is adsorbed by the addition of the unique liquid sorbent of the invention. After centrifugation, the supernatant containing the $^{125}$I-T3 bound to serum proteins is decanted, and the pellet containing the free $^{125}$I-T3 is counted in a gamma radiation counter. The amount of $^{125}$I-T3 taken up by the adsorbent is inversely related to the degree of saturation of the binding proteins. In hypothyroidism, the binding proteins are relatively unsaturated due to the low levels of the thyroid hormones. Therefore, a hypothyroid sample would result in a low T3 uptake (T3U) since the serum binding proteins would bind a large amount of the labelled T3. The reverse is true in hyperthyroidism; the percent uptake will be higher since the binding proteins are relatively saturated by the increased amount of the circulating thyroid hormones.

A typical test procedure using the test kit described above is as follows:

1. The T3 uptake kit should be removed from storage (presuming storage at 2° to 5° C.) and allowed to equilibrate to room temperature (30–45 minutes).
2. While the reagents are equilibrating to room temperature, label in duplicate 12×75 ml test tubes as follows: Normal Human Serum Control, Patient Sera, Control Sera (C.S.) and Total Counts (T.C.).
3. Add 100 microliters of Normal Human Serum Control to the appropriate tubes.
4. Add 100 ml of each of the patient samples and control sera to the appropriate tubes.
5. Add 1.0 ml of the $^{125}$I-T3 buffer to all the tubes.
6. Shake or invert the bottle of adsorbent vigorously or until all material is resuspended (15–20 times) and immediately add 1.0 ml to all tubes except the total counts. Vortex all tubes and let stand for at least 15 minutes, but no longer than 2 hours.
7. Centrifuge all of the tubes, except the T.C. for 5 minutes at 1400 g (approx. 2600 rpm).
8. Aspirate or decant (with careful blotting of the test tube rim) the supernatant, without disturbing the pellet, and count each tube for 10 seconds with a gamma radiation counter, or for a length of time sufficient to minimize counting error.

The T3 uptake ratio and the percent T3 uptake may be calculated, utilizing the test results obtained in accordance with the invention, as follows:

A. T3 UPTAKE RATIO

1. Average the 10 second or equivalent counts per unit of time of each tube and label as follows:

| | |
|---|---|
| Patient Sample | P |
| Normal Serum Control | N |
| Background of Counter | B |

2. Using the average counts from above, the T3 uptake ratio is calculated by using the following formula:

T3 Uptake Ratio=(P−B/N−B)

B. PERCENT T3 UPTAKE

1. Standardized Reference Control Percent T3 Uptake.

This method utilizes the established normal human reference value in the calculation which corrects for any variance in performing the method.

a. Average the 10 second or equivalent counts per unit of time of each tube and label as follows:

| | |
|---|---|
| Patient Sample | P |
| Normal Serum Control | N |
| Background of Counter | B | b. Using the average counts from above, the percent T3 uptake is calculated by using the following formula:

% T3 Uptake=(P−B/N−B)×% T3U of Normal Serum Control

2. Percent T3 Uptake from Total Counts a. Average the 10 second or equivalent counts per unit of time and label as follows:

| | |
|---|---|
| Patient Sample | P |
| Normal Serum Control | N |
| Background of Counter | B |
| Total Counts | TC | b. Using the average counts from above, the percent T3 uptake is calculated by using the following formula:

% T3 Uptake = (P−B/TC−B) × 100.

The following table gives sample calculations for illustrative purposes:

TABLE 1
Sample Calculations

| Sample Description | Counts/10 Sec. Corr. for Bkg. | Av. Counts/ 10 Sec. | T3U Ratio | % T3U Norm. Serum Cont. | % T3U |
|---|---|---|---|---|---|
| Total Counts | 29696 29930 | 29813 | | | |
| Normal Serum Control | 7055 6854 | 6954 | | | 23.32 |
| Hyland A Lot No. 3512NOO2AA | 5078 4969 | 5023 | .72 | 16.84 | 16.85 |
| Hyland B Lot No. 3513LOO3AA | 6800 7002 | 6901 | .99 | 23.14 | 23.15 |
| Hyland C Lot No. 3514NOO1AA | 12205 12434 | 12319 | 1.77 | 41.31 | 41.32 |

(The Hyland A, B, and C control sera referred to hereinafter are from the foregoing lots, unless otherwise stated.)

$$\text{T3U Ratio} = \frac{P - B}{N - B}$$

$$\text{T3U Ratio} = \frac{5023}{6954} = .72$$

$$\% \text{ T3U Normal Serum Control} = \frac{P - B}{N - B} \times \% \text{ T3U of Normal Serum Control}$$

$$\% \text{ T3U Normal Serum Control} = \frac{5023}{6954} \times 23.32 = 16.84$$

$$\% \text{ T3U from Total Counts} = \frac{P - B}{TC - B} \times 100$$

$$\% \text{ T3U from Total Counts} = \frac{5023}{29813} \times 100 = 16.85$$

The following table gives the result of a normal range study conducted on various clinically diagnosed samples, using the test kit.

TABLE 2
Results of Normal Range Study Conducted On Various Clinically Diagnosed Samples

| Clinical Diagnosis | Mean ± S.D. T3U Ratio | Mean ± S.D. % T3U | Mean ± S.D. T4μg/dl | Range T4* μg/dl |
|---|---|---|---|---|
| Euthyroid | 1.09±0.124 | 25.75±2.83 | 7.8±1.7 | 4.4–11.2 |
| Hypothyroid | 0.77±0.08 | 17.25±1.88 | 1.7±1.6 | |
| Hyperthyroid | 1.78±0.03 | 42.15±6.86 | 17.9±4.0 | |
| Pregnant | 0.57 ±0.06 | 13.68±1.24 | 12.5±3.0 | |

S.D. = Standard deviation of the mean
*T4 values determined by using Meloy Immunostat® RIA Kit In the following table a suggested normal range for the T3U ratio, % T3U, and FTI (Product of the T4 range and the T3 ratio range) is given. However, due to the geographical variations in iodine intake that may contribute to variations in thyroid hormone levels, it is preferred that each laboratory conduct studies to determine whether the suggested normal range is appropriate for the population it serves.

TABLE 3
Suggested Normal Range of T3 Uptake Determined For Various Thyroid States

| Clinical Diagnosis | T3U Ratio | % T3U | FTI |
|---|---|---|---|
| Hypothyroid | <0.84 | <20.0 | <3.7 |
| Euthyroid | 0.84–1.3 | 20.0–31.0 | 3.7–14.56 |
| Hyperthyroid | >1.3 | >31.0 | >14.6 |

The precision of a T3 uptake kit employing the sorbent of the invention was evaluated by using representative kits and testing a panel of control sera in the hypo-, eu-, and hyper-thyroid ranges. The following tables give the results of those tests.

TABLE 4
The Intra-Assay Variance Was Obtained by Assaying a Panel of Commercial Control Sera as Single Determinations with Three Lots of Materials
1. Intra-Assay Variance

| Serum Sample | | Runs 1 | 2 | 3 | 4 |
|---|---|---|---|---|---|
| Hypothyroid Hyland Q-Pak® A Lot #3512NOO2AA | N | 10 | 10 | 10 | 10 |
| | T3U Ratio | 0.74 | 0.74 | 0.74 | 0.74 |
| | S.D. | 0.02 | 0.02 | 0.01 | 0.01 |
| | C.V. | 2.7 | 2.7 | 1.3 | 1.3 |
| | % T3U | 16.23 | 15.21 | 17.72 | 17.52 |
| | S.D. | 0.34 | 0.41 | 0.30 | 0.27 |
| | C.V. | 2.09 | 2.69 | 1.71 | 1.55 |
| Euthyroid Hyland Q-Pak® B Lot #3513LOO3AA | N | 10 | 10 | 10 | 10 |
| | T3U Ratio | 1.02 | 1.03 | 1.01 | 1.02 |
| | S.D. | 0.02 | 0.02 | 0.01 | 0.01 |
| | C.V. | 1.96 | 1.94 | 0.99 | 9.98 |
| | % T3U | 22.55 | 21.01 | 23.64 | 24.1 |
| | S.D. | 0.45 | 0.35 | 0.32 | 0.29 |
| | C.V. | 1.99 | 1.66 | 1.38 | 1.23 |
| Hyperthyroid Hyland Q-Pak® C Lot #3514NOO1AA | N | 10 | 10 | 10 | 10 |
| | T3U Ratio | 1.72 | 1.83 | 1.63 | 1.73 |
| | S.D. | 0.02 | 0.03 | 0.016 | 0.01 |
| | C.V. | 1.16 | 1.64 | 0.99 | 0.58 |
| | % T3U | 38.05 | 37.39 | 38.28 | 40.72 |
| | S.D. | 0.45 | 0.55 | 0.37 | 0.44 |
| | C.V. | 1.19 | 1.49 | 0.97 | 1.09 |

N = Number of determinations
S.D. = Standard deviation of the mean
C.V. = Coefficient of variation (%)

TABLE 5
The Inter-Assay Variance Was Obtained by Assaying a Panel of Control Sera in Duplicate in at Least 39 Runs.
2. Inter-Assay Variance

| Serum Sample | No. of Runs | Mean T3U Ratio | S.D. | C.V. | Mean % T3U | S.D. | C.V. |
|---|---|---|---|---|---|---|---|
| Hypothyroid Hyland Q Pak® A Lot #3512NOO2AA | 39 | 0.74 | 0.027 | 3.65 | 17.24 | 1.31 | 7.60 |
| Euthyroid Hyland Q Pak® B Lot #3513LOO3AA | 39 | 1.01 | 0.044 | 4.37 | 23.40 | 1.66 | 7.11 |
| Hyperthyroid Hyland Q Pak® C | 39 | 1.71 | 0.065 | 3.78 | 39.74 | 1.87 | 4.70 |

TABLE 5-continued

The Inter-Assay Variance Was Obtained by Assaying a
Panel of Control Sera in Duplicate in at Least 39 Runs.

2. Inter-Assay Variance

| Serum Sample | No. of Runs | Mean T3U Ratio | S.D. | C.V. | Mean % T3U | S.D. | C.V. |
|---|---|---|---|---|---|---|---|
| Lot #3514NOO1AA | | | | | | | |

S.D. = Standard deviation of the mean
C.V. = Coefficient of variation (%)

Extensive tests were conducted to determine, inter alia, comparative performance of the clay-organic complexes in accordance with the invention versus bentonite (believed to be the closest sorbent of the prior art), comparative performance of different clay-organic complexes, the effects of adding gums to the sorbents, the effects of serum sample size, the effects of concentration of the sorbent, the effects of incubation (equilibration) time, the effects of temperature, the reproducibility of T3 uptake tests employing the invention, and the effects of pH. These tests are illustrated by the following examples.

EXAMPLE 1

In this example an assay was performed by adding 0.1 ml of patient's serum sample to 1 ml of radioactive T3 trace in barbital buffer; adding 1.0 ml of sorbent suspended in barbital buffer, incubating for 15 minutes, centrifuging at 2600 rpm for 5 minutes, decanting, and counting the radioactivity of the pellet (containing the unbound T3). The buffer employed was 0.05 M sodium barbital, pH 8.6, containing 0.1% sodium azide preservative (and 0.02% albumin in the trace buffer). The sorbent was prepared from the commercially available Bentone 14 as described earlier and was then added to the mixture of serum sample and T3 trace, after which the mixture was vortexed for 5 seconds. The radioactive isotope of choice, and the isotope employed, was $^{125}I$, which has a stability of 85 days and a half life of 60 days. However, other isotopes of iodine, tritium, carbon, nitrogen or selenium could be utilized. Also, other molarity barbitals as well as other buffer systems, such as sodium or potassium phosphates or tris (tris-hydroxymethyl aminomethane) could be employed.

Table 6 is a comparison of test results obtained utilizing a sorbent of the invention (Bentone 14 in this example) versus the results obtained utilizing bentonite. The table shows the improved separation of thyroid states, particularly between hypothyroid and normal states in this example, achieved by the utilization of the invention. The sorbent of the invention in this example included 0.2% Jaguar A2S gum. Samples of bentonite with and without the gum were used for comparison. The improved results of the invention were achieved with a smaller sorbent concentration, 3.0 mg/ml for the Bentone 14 versus 20.0 mg/ml for bentonite. When smaller (or larger) concentrations of bentonite were tried, the separation of thyroid states was inferior to (or no better than) the separation achieved with a bentonite concentration of 20.0 mg/ml.

TABLE 6

Comparison of Bentone-14 vs. Bentonite
% T3U

| | 3.0 mg/ml BENTONE 0.2% A2S | 20.0 mg/ml BENTONITE | 20.0 mg/ml BENTONITE 0.2% A2S |
|---|---|---|---|
| Hypothyroid Hyland Q-Pak ® "A" | 18.38 | 39.41 | 28.47 |
| Normal Hyland Q-Pak ® "B" | 25.06 | 42.11 | 31.11 |
| Hyperthyroid Hyland Q-Pak ® "C" | 40.56 | 57.09 | 43.67 |
| | T3U Ratio | | |
| Hypothyroid (Hyland A) | .73 | .94 | .92 |
| Hyperthyroid (Hyland C) | 1.62 | 1.35 | 1.41 |

EXAMPLE 2

In this example the utility of various organically modified montmorillonites as sorbents in a T3 uptake test is shown. The basic test was conducted as in Example 1 except that the slurries of the sorbents did not contain gums, necessitating constant mixing of the sorbents with a magnetic stir bar during the addition stage. To illustrate the usefulness of the sorbents in the invention, experiments were conducted utilizing normal, hypothyroid, and hyperthyroid patient serum samples.

TABLE 7

BENTONE 14

In this test 0.1 milliliter of each control serum was added to 1.0 ml of barbital diluted $^{125}I$-T3 tracer. Then 1.0 ml of a 4.0 mg/ml dispersion of Bentone 14 was added. The results in percent uptake and uptake ratio are:

| Sample | % T3 Uptake | T3 Uptake Ratio |
|---|---|---|
| HYPOTHYROID (Hyland A) | 26.39 | .86 |
| NORMAL (Hyland B) | 35.75 | |
| HYPERTHYROID (Hyland C) | 51.22 | 1.41 |

TABLE 8

BENTONE 27

In this test 0.1 milliliter of each control serum was added to 1.0 ml of barbital diluted $^{125}I$-T3 tracer. Then 1.0 ml of a 5.0 mg/ml dispersion of Bentone 27 was added.
The results in percent uptake and uptake ratio are:

| Sample | % T3 Uptake | T3 Uptake Ratio |
|---|---|---|
| HYPOTHYROID (Hyland A) | 41.44 | .86 |
| NORMAL (Hyland B) | 48.10 | |
| HYPERTHYROID (Hyland C) | 67.45 | 1.41 |

TABLE 9
BENTONE 34

In this test 0.1 milliliter of each control serum was added to 1.0 ml of barbital diluted $^{125}$I-T3 tracer. Then 1.0 ml of a 1.5 mg/ml dispersion of Bentone 34 was added. The results in percent uptake and uptake ratio are:

| Sample | % T3 Uptake | T3 Uptake Ratio |
|---|---|---|
| HYPOTHYROID (Hyland A) | 23.70 | .87 |
| NORMAL (Hyland B) | 27.18 | |
| HYPERTHYROID (Hyland C) | 45.49 | 1.67 |

TABLE 10
BENTONE 38

In this test 0.1 milliliter of each control serum was added to 1.0 ml of barbital diluted $^{125}$I-T3 tracer. Then 1.0 ml of a 3 mg/ml dispersion of Bentone 38 was added. The results in percent uptake and uptake ratio are:

| Sample | % T3 Uptake | T3 Uptake Ratio |
|---|---|---|
| HYPOTHYROID (Hyland A) | 17.30 | .82 |
| NORMAL (Hyland B) | 21.24 | |
| HYPERTHYROID (Hyland C) | 40.75 | 1.92 |

TABLE 11
RHEOTONE SA-38

In this test 0.1 milliliter of each control serum was added to 1.0 ml of barbital diluted $^{125}$I-T3 tracer. Then 1.0 ml of a 2 mg/ml dispersion of Rheotone SA-38 was added. The results in percent uptake and uptake ratio are:

| Sample | % T3 Uptake | T3 Uptake Ratio |
|---|---|---|
| HYPOTHYROID (Hyland A) | 30.99 | .83 |
| NORMAL (Hyland B) | 37.36 | |
| HYPERTHYROID (Hyland C) | 58.33 | 1.56 |

The above data clearly shows the improved separation of thyroid states achieved by the use of organically modified montmorillonites and also shows, incidentally, the utility of different concentrations of the clay-organic complexes.

EXAMPLE 3

In this example various guar gums were added to the sorbent mixture to increase the viscosity of the mixture and thereby to avoid the need for constant mixing. Jaguar gums marketed by Stein, Hall and Co., Inc. of New York were used. The various gums were added to buffered Bentone 38 (3.0 mg/ml) as described previously. The experiment was conducted, generally as set forth in Example 1, to determine the effect of the gums on the T3 uptake test performance.

TABLE 12

| | BENTONE 14 | | | | | |
|---|---|---|---|---|---|---|
| | Jaguar A2S (0.2% solution) | | Jaguar HP-11 (0.2% solution) | | Jaguar A4OF (0.2% solution) | |
| Sample | % T3U | T3 Ratio | % T3U | T3 Ratio | % T3U | T3 Ratio |
| HYPOTHYROID (Hyland A) | 23.21 | .74 | 23.5 | .73 | 24.75 | .76 |
| NORMAL (Hyland B) | 31.29 | | 32.01 | | 32.53 | |
| HYPERTHYROID (Hyland C) | 46.68 | 1.49 | 45.56 | 1.54 | 46.27 | 1.42 |

TABLE 13

| | BENTONE 38 | | | | | |
|---|---|---|---|---|---|---|
| | Jaguar A2S (0.2% solution) | | Jaguar HP-11 (0.2% solution) | | Jaguar A4OF (0.2% solution) | |
| Sample | % T3U | T3 Ratio | % T3U | T3 Ratio | % T3U | T3 Ratio |
| HYPOTHYROID (Hyland A) | 29.27 | .78 | 24.97 | .78 | 26.80 | .81 |
| NORMAL (Hyland B) | 37.20 | | 32.07 | | 33.06 | |
| HYPERTHYROID (Hyland C) | 56.39 | 1.52 | 51.45 | 1.61 | 51.69 | 1.56 |

The above data shows that the guar gums, when added to the clay-organic sorbents employed in the invention, do not significantly affect the separating ability of the sorbents.

EXAMPLE 4

A test was conducted to determine the effect on performance of settling of a sorbent-gum mixture. This test was conducted as described in Example 1. Samples of the sorbent-gum mixture (3.0 mg/ml Bentone 14 with 0.2% Jaguar gum A2S) were mixed by shaking and were added to normal human samples at 0, 2, 5, 7, 10, 15, 20, and 30 minutes after shaking.

TABLE 14

| Settling Time (minutes) | % T3 Uptake |
|---|---|
| 0 | 23.5 |
| 2 | 22.7 |
| 5 | 22.4 |
| 7 | 23.3 |
| 10 | 22.3 |
| 15 | 23.7 |
| 20 | 23.5 |
| 30 | 20.8 |

This data shows that the addition of guar gums to the clay-organic sorbent keeps the material suspended in the buffer for at least 20 minutes without affecting the results of the T3 uptake test. This allows the sorbent material to be added without constant mixing. Without the addition of the gum, the sorbent settles out of the buffer in 2 to 5 minutes, which necessitates constant mixing during addition.

EXAMPLE 5

This example shows the effect of serum sample size. A 3.0 mg/ml Bentone 14 sorbent with 0.2% Jaguar gum A2S was used with different serum sample sizes. The test was conducted as set forth in Example 1.

TABLE 15
0.2 ml Sample Size 0.2 milliliters of sample were added to 1.0 ml of $^{125}$I-T3 trace and then 1.0 ml of the organic sorbent as described above.

| Sample | % T3 Uptake | T3 Ratio |
|---|---|---|
| HYPOTHYROID (Hyland A) | 10.29 | .83 |
| NORMAL (Hyland B) | 12.26 | |
| HYPERTHYROID (Hyland C) | 18.88 | 1.54 |

TABLE 16
0.1 ml Sample Size 0.1 milliliters of sample were added to 1.0 ml of $^{125}$I-T3 trace and then 1.0 ml of the organic sorbent as described above.

| Sample | % T3 Uptake | T3 Ratio |
|---|---|---|
| HYPOTHYROID (Hyland A) | 16.78 | .76 |
| NORMAL (Hyland B) | 21.92 | |
| HYPERTHYROID (Hyland C) | 36.50 | 1.66 |

TABLE 17
0.05 ml Sample Size 0.05 milliliters of sample were added to 1.0 ml of $^{125}$I-T3 trace and then 1.0 ml of the organic sorbent as described above.

| Sample | % T3 Uptake | T3 Ratio |
|---|---|---|
| HYPOTHYROID (Hyland A) | 28.86 | .83 |
| NORMAL (Hyland B) | 34.59 | |
| HYPERTHYROID (Hyland C) | 46.52 | 1.34 |

TABLE 18
0.025 ml Sample Size 0.025 milliliters of sample were added to 1.0 ml of $^{125}$I-T3 trace and then 1.0 ml of the organic sorbent as described above.

| Sample | % T3 Uptake | T3 Ratio |
|---|---|---|
| HYPOTHYROID (Hyland A) | 44.93 | .82 |
| NORMAL (Hyland B) | 54.17 | |
| HYPERTHYROID (Hyland C) | 61.04 | 1.12 |

TABLE 19
0.01 ml Sample Size 0.01 milliliters of sample were added to 1.0 ml of $^{125}$I-T3 trace and then 1.0 ml of the organic sorbent as described above.

| Sample | % T3 Uptake | T3 Ratio |
|---|---|---|
| HYPOTHYROID (Hyland A) | 66.26 | .93 |
| NORMAL (Hyland B) | 70.78 | |
| HYPERTHYROID (Hyland C) | 75.53 | 1.06 |

From the above data, it is apparent that when 3.0 mg/ml Bentone 14 sorbent is employed, the best separation of the three thyroid states is achieved with a 0.1 ml sample size. If a smaller sample size is desired, the optimum concentration of the sorbent can be determined empirically. As an example, a 0.01 ml sample size requires a Bentone 14 concentration of 0.3 to 0.5 mg/ml for optimum separation of the three thyroid states.

EXAMPLE 6

In this example, a test was conducted to ascertain the effect of sorbent concentration on the T3 uptake test results. The test was run as set forth in Example 1, but with different concentrations of Bentone 27 in this instance.

TABLE 20

| Sample | BENTONE 27 (1 mg/ml) | | BENTONE 27 (5 mg/ml) | |
|---|---|---|---|---|
| | % T3U | T3 Ratio | % T3U | T3 Ratio |
| HYPOTHYROID (Hyland A) | 13.16 | .78 | 41.44 | .86 |
| NORMAL (Hyland B) | 16.72 | | 48.10 | |
| HYPERTHYROID (Hyland C) | 28.65 | 1.72 | 67.45 | 1.41 |

This data shows that different concentrations of the clay-organic sorbents may be employed in a T3 uptake test to optimize the clinical diagnosis. Each sorbent concentration should be optimally determined to achieve the best separation of the three thyroid states.

EXAMPLE 7

In this test the effects of incubation time on the sorbent were evaluated. The test was conducted by incubating Bentone 14 containing 3 mg/ml of 0.2% Jaguar gum A2S for different incubation times before centrifugation, and then the samples were processed as previously in Example 1.

TABLE 21

| Incubation Time | % T3 Uptake |
|---|---|
| 0 | 18.32 |
| 5 | 21.95 |
| 10 | 24.18 |
| 15 | 27.8 |
| 30 | 28.10 |
| 45 | 28.40 |
| 60 | 28.43 |
| 90 | 28.64 |
| 120 | 28.25 |

This test clearly indicates that the incubation period is not critical after 15 minutes.

EXAMPLE 8

In this test the effects of temperature T3 uptake test results were determined. The test was performed as in Example 1.

TABLE 22

| | % T3U | | |
|---|---|---|---|
| Temperature | Hyland A | Hyland B | Hyland C |
| 20° C. | 15.2 | 21.0 | 37.4 |
| 20.4 | 15.5 | 21.5 | 37.0 |
| 20.8 | 15.7 | 22.0 | 36.9 |
| 21.0 | 16.5 | 22.1 | 38.9 |
| 21.5 | 17.3 | 23.1 | 39.4 |
| 22.0 | 17.3 | 23.3 | 38.9 |

TABLE 22-continued

| | % T3U | | |
|---|---|---|---|
| Temperature | Hyland A | Hyland B | Hyland C |
| 23.0 | 16.6 | 22.6 | 39.5 |
| 24.0 | 17.7 | 23.6 | 38.5 |
| 24.4 | 17.4 | 23.0 | 38.5 |
| 24.8 | 18.6 | 25.7 | 41.6 |
| 25.8 | 18.8 | 25.2 | 41.6 |

TABLE 23

| | T3U Ratio | |
|---|---|---|
| Temperature | Hyland A | Hyland C |
| 20° C. | .73 | 1.78 |
| 20.4 | .72 | 1.72 |
| 20.8 | .72 | 1.68 |
| 21.0 | .75 | 1.76 |
| 21.5 | .75 | 1.71 |
| 22.2 | .74 | 1.67 |
| 23.0 | .73 | 1.75 |
| 24.0 | .75 | 1.63 |
| 24.4 | .76 | 1.67 |
| 24.8 | .72 | 1.62 |
| 25.8 | .75 | 1.65 |

It is apparent that effects of temperature within the usual temperature range encountered in laboratories are within the permissible assay variance ranges. Moreover, the effects of temperature are negated in the T3U ratio computation.

EXAMPLE 9

The reproducibility of the T3 uptake test using the procedure set forth in Example 1 was determined by analyzing 10 samples of the same serum. The test results are as follows:

TABLE 24

| Sample | % T3 Uptake |
|---|---|
| 1 | 27.23 |
| 2 | 26.17 |
| 3 | 26.39 |
| 4 | 25.95 |
| 5 | 25.79 |
| 6 | 26.77 |
| 7 | 26.32 |
| 8 | 26.46 |
| 9 | 25.81 |
| 10 | 25.57 |

This data shows that the test results are very reproducible.

EXAMPLE 10

Comparative tests were performed to determine the effect of pH on the T3 uptake test. The pH of the buffered radioactive trace was adjusted to that indicated, and then the sorbent was added and the assay conducted as set forth in Example 1. To obtain a pH of 9.7 and higher, sodium hydroxide was added to barbituric acid.

TABLE 25

| | Bentone 14 at 3 mg/ml 0.2% Jaguar Gum A2S | | | | | |
|---|---|---|---|---|---|---|
| | % T3U | | | | | |
| Sample | pH 6.5 | pH 7.5 | pH 8.5 | pH 9.7 | pH 10.7 | pH 11.2 |
| Hyland A Lot #3512NOO3A | 30.8 | 29.5 | 21.1 | 19.2 | 18.4 | 5.1 |
| Hyland B Lot #3513NOO1A | 35.9 | 35.0 | 24.3 | 24.5 | 23.7 | 5.6 |
| Hyland C Lot #3514NOO2A | 47.8 | 46.4 | 34.9 | 33.8 | 31.4 | 5.1 |

| | % T3U Ratio | | | | | |
|---|---|---|---|---|---|---|
| Hyland A | .85 | .84 | .87 | .78 | .78 | 1.0 |
| Hyland C | 1.33 | 1.32 | 1.43 | 1.40 | 1.33 | .90 |

It is apparent that satisfactory separation of thyroid states is achieved in the pH range of from about 6.5 to 10.7, with barbital buffer. With other buffers, satisfactory results may be achieved with a lower pH.

It is apparent that the invention provides significant improvements in T3 uptake and similar tests.

While preferred embodiments of the invention have been shown and described, it will be apparent to those skilled in the art that changes can be made in these embodiments without departing from the principles and spirit of the invention, the scope of which is defined in the appended claims. For example, the sorbent employed in the invention may be tableted and later suspended in a buffer for use.

I claim:

1. In a test for assessing the unsaturated binding capacity of serum proteins which bind thyroid hormones and in which a radioactive thyroid hormone is admixed with a serum sample, free radioactive hormone is adsorbed by a sorbent added to the mixture, the adsorbed and non-adsorbed fractions are separated, and the radioactivity of the adsorbed or non-adsorbed fraction is determined, the improvement wherein the sorbent comprises a montmorillonite-ammonium complex.

2. A test in accordance with claim 1, wherein the complex is produced by adding an amine salt or a quaternary ammonium salt or base to a clay-water suspension and exchanging organic cations for exchangeable cations on the clay surfaces.

3. A test in accordance with claim 1, wherein the complex is selected from the group consisting of a triaalkylaryl ammonium smectite and a tetraalkyl ammonium smectite.

4. A test in accordance with claim 1, wherein the sorbent is added in the form of a dispersion.

5. A test in accordance with claim 4, wherein the complex is dispersed in a buffer.

6. A test in accordance with claim 5, wherein the pH of the buffer is between about 6.5 and about 10.7.

7. A test in accordance with claim 1, wherein the sorbent is added in a dispersion with a concentration in the range of from a fraction of a mg/ml to several mg/ml.

8. A test in accordance with claim 1, wherein the sorbent is added in a dispersion and is admixed with an agent for maintaining the complex in suspension.

9. A test in accordance with claim 8, wherein the agent is a guar gum.

10. In a test kit for measuring T3 uptake and including packaged units of T3 uptake normal human control serum and radioactive T3 buffer reagent, the improvement comprising, as part of the test kit, a packaged unit of a sorbent comprising an organically modified montmorillonite constituting a montmorillonite-ammonium complex.

11. A test kit in accordance with claim 10, wherein the sorbent comprises a complex selected from the group consisting of a trialkylaryl ammonium smectite and a tetraalkyl ammonium smectite.

12. A test kit in accordance with claim 10, wherein the organically modified montmorillonite is in a dispersion.

13. A test kit in accordance with claim 10, wherein the organically modified montmorillonite is dispersed in a buffer having a pH between about 6.5 and about 10.7.

14. A test kit in accordance with claim 13, wherein the concentration of the organically modified montmorillonite is in the range of from a fraction of a mg/ml to several mg/ml.

15. A test kit in accordance with claim 10, wherein the organically modified montmorillonite is admixed with a gum in a dispersion.

16. A test kit in accordance with claim 15, wherein the gum is a guar gum.

* * * * *